United States Patent [19]

Rice et al.

[11] Patent Number: 5,668,285
[45] Date of Patent: Sep. 16, 1997

[54] TOTAL SYNTHESIS OF NORTHEBAINE, NORMOPHINE, NOROXYMORPHONE ENANTIOMERS AND DERIVATIVES VIA N-NOR INTERMEDIATES

[75] Inventors: Kenner C. Rice, Bethesda; Amy H. Newman, Silver Spring, both of Md.

[73] Assignee: The United States of America as represented by the Department of Health and Human Services, Washington, D.C.

[21] Appl. No.: 851,672

[22] Filed: Mar. 12, 1992

Related U.S. Application Data

[63] Continuation-in-part of Ser. No. 421,900, Oct. 16, 1989, abandoned, which is a continuation-in-part of Ser. No. 925,620, Oct. 31, 1986, abandoned.

[51] Int. Cl.$^6$ .................................................. C07D 489/02
[52] U.S. Cl. ............................................. 546/44; 546/149
[58] Field of Search ....................... 546/44, 45; 514/282

[56] References Cited

U.S. PATENT DOCUMENTS

| | | | |
|---|---|---|---|
| 3,299,072 | 1/1967 | Bartels-Keith | 546/44 |
| 3,896,226 | 7/1975 | Fishman | 546/66 X |
| 4,141,897 | 2/1979 | Olofson et al. | 546/44 |
| 4,368,326 | 1/1983 | Rice | 546/45 |
| 4,472,253 | 9/1984 | Schwartz | 546/45 X |
| 4,521,601 | 6/1985 | Rice | 546/45 |
| 4,613,668 | 9/1986 | Rice | 546/44 |
| 4,639,520 | 1/1987 | Kavka | 546/45 |
| 5,071,985 | 12/1991 | Andre et al. | 546/44 |

FOREIGN PATENT DOCUMENTS

| | | | |
|---|---|---|---|
| 0913077 | 10/1972 | Canada | 546/44 |
| 0158476 | 10/1985 | European Pat. Off. | 546/45 |
| 2208902 | 8/1974 | France | 546/45 |
| 60-226889 | 11/1985 | Japan | |
| 60-218392 | 11/1986 | Japan | |
| WO/80/00841 | 5/1980 | WIPO | 546/45 |
| WO81/00409 | 2/1981 | WIPO | 546/45 |

OTHER PUBLICATIONS

Bartels–Keith, J. Chem. Soc.,(C), pp. 617–624 (1966).
Rice, Chemical Abstracts, vol. 101:55403t(1984) Abstract of U.S. Pat. Appl. US 564,515 Apr. 13, 1984, avail NTIS Order No. PAT-APPL-6-564 515.
Rice, J. Org. Chem., vol. 45(15), pp. 3135–3137 (Jul. 18, 1980).
Speyer, et al., Berichte, 57, pp. 1427–1430 (1924), note attached pp. 258, 262, of Bentley, The Chemistry of the Morphine Alkaloids, Oxford, Clarendon Press (1954).
Currie, et al. (I), Chemical Abstracts, vol. 56:11638b–11639h (1962).
Currie, et al. (II), Chemical Abstracts, vol. 62: 2801h–2802–2802c (1965).

*Primary Examiner*—Donald G. Daus
*Attorney, Agent, or Firm*—Birch, Stewart, Kolasch & Birch, LLP

[57] ABSTRACT

The invention involves a method of making key intermediates useful in the synthesis of many opiate narcotics and antagonists and agonists; and the non-opiate enantiomers thereof which have potent antitussive properties. The synthesis starts from either the natural or unnatural enantiomer of nordihydrocodeinone and produces 8, 14-dihydronorthebaine, the diketal of 7-bromonordihydrocodeinone, northebaine, norcodeinone diketal and 14-hydroxynorcodeinone intermediates without the necessity of leaving the N-nor structure. The syntheses have fewer steps than previous methods, and also have high yields.

20 Claims, No Drawings

TOTAL SYNTHESIS OF NORTHEBAINE, NORMOPHINE, NOROXYMORPHONE ENANTIOMERS AND DERIVATIVES VIA N-NOR INTERMEDIATES

CHART 1: KEY INTERMEDIATES IN THE TOTAL SYNTHESIS OF CODEINE, MORPHINE AND THEBAINE (APPLICABLE TO BOTH THE NATURAL AND UNNATURAL SERIES)

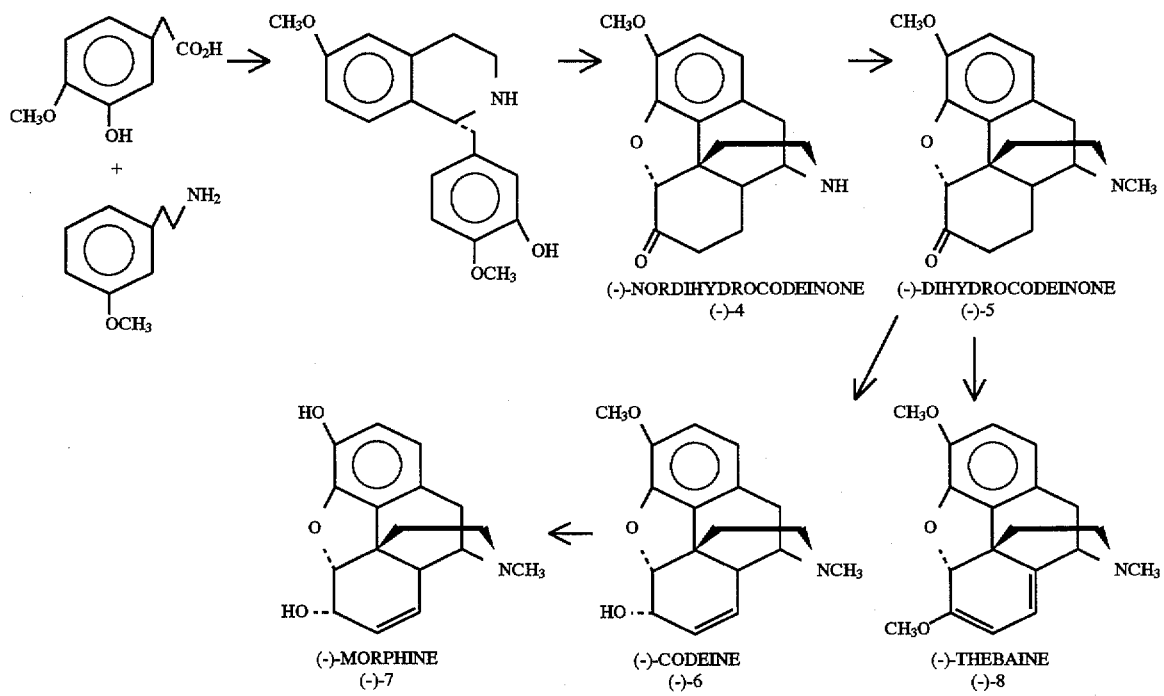

BACKGROUND OF THE INVENTION

1. Field of the Invention

This is a continuation-in-part application of U.S. patent application Ser. No. 07/421,900 filed Oct. 16, 1989, now abandoned, the entire contents of which are hereby incorporated by reference, which is a continuation-in-part of U.S. patent application Ser. No. 06/925,620 filed Oct. 31, 1986, now abandoned, the entire contents of which are hereby incorporated by reference.

The present invention relates to a total synthesis method proceeding from nordihydrocodeinone. A significant aspect associated with the present invention is that a facile method has now been developed, utilizing N-Nor intermediates throughout, for conversion of nordihydrocodeinone to northebaine, noroxymorphone, norcodeine, normophine and derivatives thereof. The present invention also pertains to the synthesis of compounds of both the natural (−)- and unnatural (+)-stereochemical series of nordihydrocodeinone.

2. Discussion of Related Art

Previous U.S. patents granted to one of the present inventors, i.e. U.S. Pat. Nos. 4,368,326 (Rice) and 4,521,601 (Rice), disclose the total synthesis of either enantiomer of nordihydrocodeinone (4) and the subsequent conversion of this compound to the N-methyl derivative, dihydrocodeinone (5), which is a useful intermediate in this context for synthesis of codeine (6), morphine (7) and thebaine (8). Chart 1 below illustrates these synthetic schemes as well as the natural stereochemistry of these compounds. The latter three compounds are the only raw materials obtained from opium which are of value in the production of narcotics, narcotic antagonists and the agonist-antagonists drugs.

In the standard manufacturing process of the narcotic antagonists, naloxone (2), naltrexone (21), nalmefene (22), and the agonist-antagonist nalbuphine (26), (−)-thebaine (8) is obtained by extraction from opium and utilized as starting material. (−)-Codeine has also been advanced as a possible starting material for these compounds. Since both natural thebaine and codeine have a methyl substituent on the nitrogen, removal of the methyl group and replacement with a cycloalkylmethyl or allyl group and other structural alterations are necessary in order to obtain the desired pharmacological profile in the final products. For example, in the synthesis of the narcotic antagonists, natural thebaine is sequentially oxidized to 14-hydroxycodeinone, reduced to 14-hydroxydihydrocodeinone, and O-demethylated to oxymorphone. The methyl group is then removed by the following sequence: acetylation to the 3,14-diacetoxy derivative, reaction with cyanogen bromide or a chloroformate ester, and hydrolyzed to noroxymorphone which is finally alkylated with the appropriate allyl halide.

A major disadvantage of the conventional commercial process is the multistep removal of the N-methyl group involving the acylation reaction, reaction with cyanogen bromide or phosgene-derived chloroformate (which are toxic and otherwise dangerous reagents), and the hydrolysis step. The hydrolysis of the N-cyano employed in the standard process requires prolonged heating with a large excess of 25% sulfuric acid that results in partial destruction of the desired noroxymorphone.

SUMMARY OF THE INVENTION

The instant invention is a process in which nordihydrocodeinone (4), an early intermediate in the total synthesis of codeine, morphine and thebaine, is converted through intermediates without substituents on the amine nitrogen atom to a number of versatile N-nor intermediates. These compounds can serve as precursors for a number of important drugs (with the natural opiate stereochemistry) currently used in the practice of medicine. The process thus eliminates the need for thebaine for the total synthesis of these drugs. Since nordihydrocodeinone is directly available by total synthesis as either the (+)- or (−)-enantiomer, optional access is provided to either the natural or unnatural opiate series. Since the N-nor intermediates can be N-alkylated at any stage to afford a desired N-substituted product, the process is much more versatile than the classical route, and substantially shorter because the N-demethylation sequence is eliminated.

For the total synthesis, the instant invention thus differs from the prior art by not utilizing thebaine, that is, it is unnecessary to introduce the methyl group onto the nitrogen atom (corresponding to the step from compound (4) to compound (5) in Chart 1) and then remove it after further transformation of thebaine. This results in a shorter and more economical process by eliminating a substantial number of steps and requirements for labor and raw materials. Furthermore, each step in the process gives very high yields and each isolated intermediate is obtained pure, or very nearly so, by advantageously simple crystallization and washing. Also, since nordihydrocodeinone (4) can now be synthesized in both the natural and unnatural series based on conventional techniques, employing the present invention advantageously allows for avoidance of the requirement to cultivate the poppy plant.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

A description of the preferred process of the present invention follows with references to Charts 2–8. As shown by the synthetic schemes in Chart 2 below, anhydrous nordihydrocodeinone (4) as either enantiomer is treated with a mixture of trialkyl orthoformate, corresponding short chain alkyl alcohol, and a phenolic sulfonic acid to give a mixture of the ketal (9) and enol ether (10). Tetrahydrofuran is added and distilled to completely convert the mixture to enol ether (10) which can be isolated in 90% yield. Treatment of the enol ether (10) in a short chain alcohol such as methanol with halogenating reagent, preferably a brominating reagent such as N-bromoacetamide and organic acid such as methanesulfonic acid gives 88% yield of crystalline bromoketal (11) as the hydrobromide. Treatment of compound (11) with a strong organic base, such as potassium t-butoxide in dimethylsulfoxide or sodium hydride, sodium amide in an aprotic polar organic solvent then gives northebaine (12) in 97% yield. Oxidation of northebaine (12) with performic acid formed in situ afforded pure 14-hydroxynorcodeinone (13) in 90% yield after crystallization from any short chain alcohol, such as methanol or other suitable purification technique. Catalytic hydrogenation of compound (13) (generally with palladium) smoothly affords crude, nearly pure noroxycodone (18) in quantitative yield. Addition of formaldehyde in this hydrogenation provides the clinically used agonist percodan (17). O-Demethylation of percodan (17) by standard procedures gives numorphan (16) also used clinically as a potent narcotic agonist. Brief treatment (O-demethylation) of compound (18) with $BBr_3$ or other standard O-demethylation procedure then gives noroxymorphone (19). Percodan (17) and numorphan (16) are also available by N-methylation of compounds (18) and (19), respectively, using standard methods.

CHART 2: SYNTHESIS OF KEY INTERMEDIATES, PERCODAN AND NUMORPHAN FROM NORDIHYDROCODEINONE. ILLUSTRATED IN THE NATURAL STEREOCHEMICAL SERIES BUT EQUALLY APPLICABLE TO THE UNNATURAL SERIES.

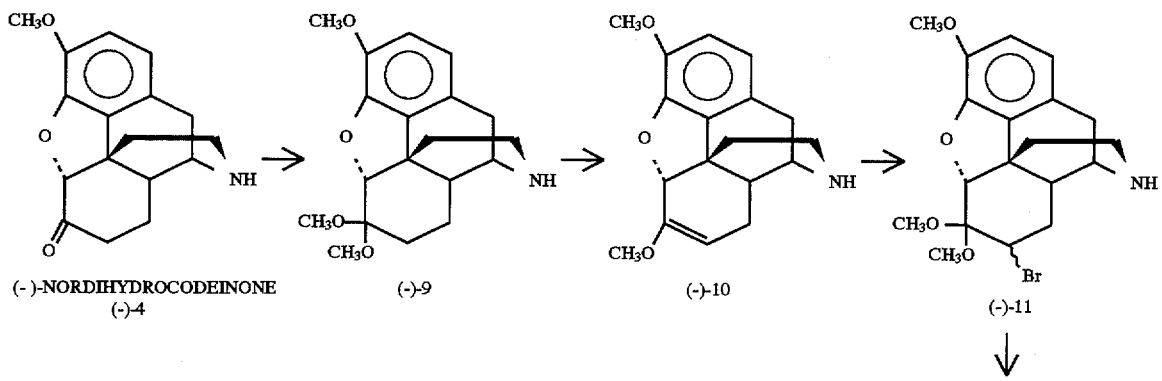

-continued
CHART 2: SYNTHESIS OF KEY INTERMEDIATES, PERCODAN AND NUMORPHAN FROM NORDIHYDROCODEINONE. ILLUSTRATED IN THE NATURAL STEREOCHEMICAL SERIES BUT EQUALLY APPLICABLE TO THE UNNATURAL SERIES.

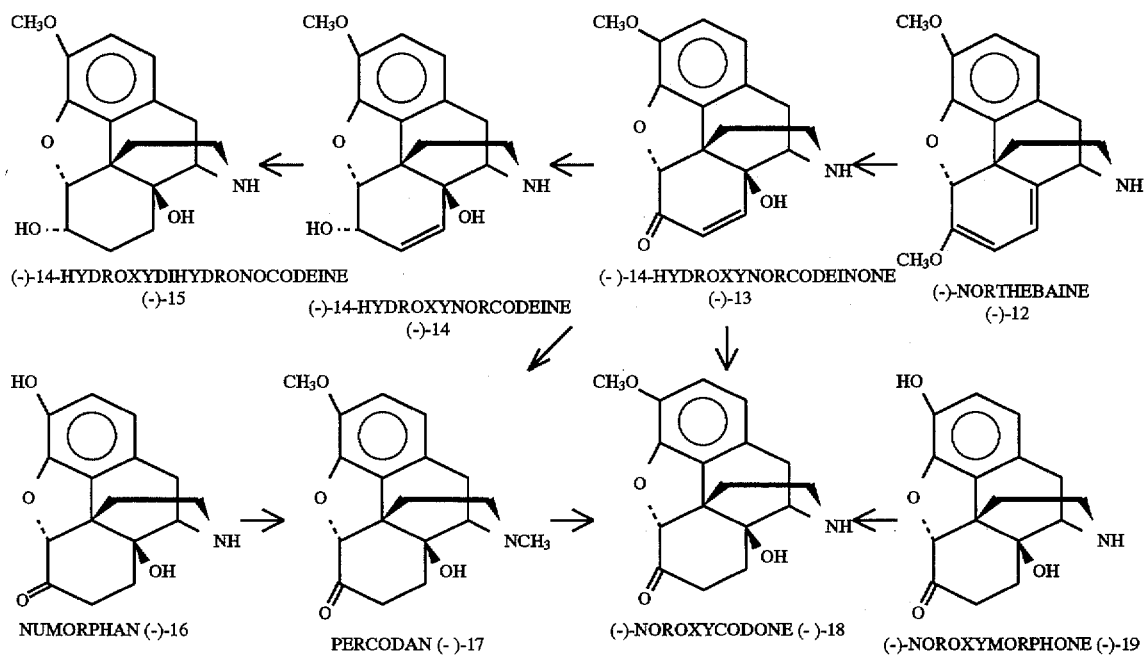

As shown in Chart 3 below, noroxymorphone (19) is a centrally important precursor for naloxone (20), naltrexone (21), nalmefene (22), all valuable narcotic antagonists in the natural stereochemical series. N-alkylation of compound (19) with allyl or cyclopropylmethyl bromide by standard methods gives naloxone and naltrexone, respectively. These compounds can also be obtained as shown in Chart 3 by alkylation of noroxycodone (18) to compounds (23) and (24), followed by O-demethylation with $BBr_3$ or other suitable reagent. Reaction of naltrexone (21) with methylene triphenylphosphorane according to standard protocol then gives nalmefene (22). Stereoselective reduction of 14-hydroxynorcodeinone (13) generally with any stereoselective reduction agent, preferably an alkali borohydride such as sodium borohydride, gives 14-hydroxynorcodeine (14) to the exclusion of the isocodeine derivative (Chart 2). Catalytic hydrogenation of compound (14), typically with palladium, provides a quantitative yield of 14-hydroxynordihydrocodeine (15).

CHART 3:

A: SYNTHESIS OF NALOXONE (20), NALTREXONE (21) AND NALMEFENE (22) FROM NOROXYMORPHINE (19)

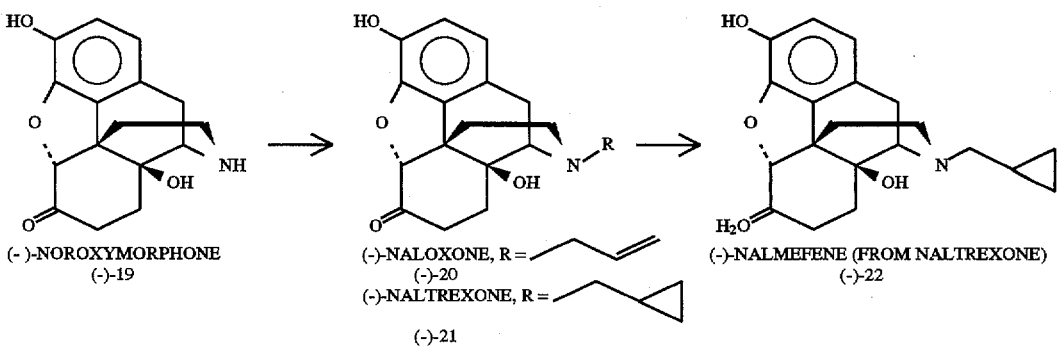

CHART 3:

B: SYNTHESIS OF NALOXONE (20), NALTREXONE (21) AND NALMEFENE (22) FROM NOROXYCODONE (18)

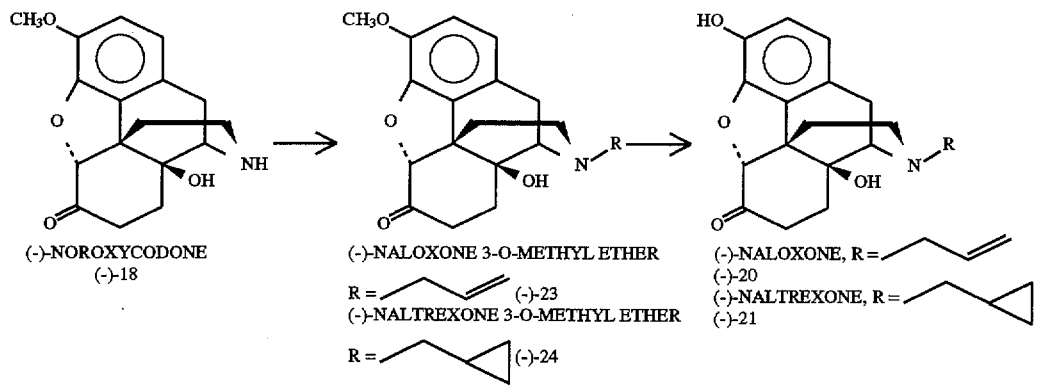

As shown in Chart 4 below, N-cyclobutyl-methylation of (15) to (25) followed by O-demethylation of (25) gives nalbuphine (26, Nubaine), a clinically useful agonist-antagonist drug. Alternately, O-demethylation of (15) to 14-hydroxydihydronormorphine (27) followed by N-cyclobutylation gives nalbuphine.

CHART 4: SYNTHESIS OF NALBUPHINE (NUBAINE)

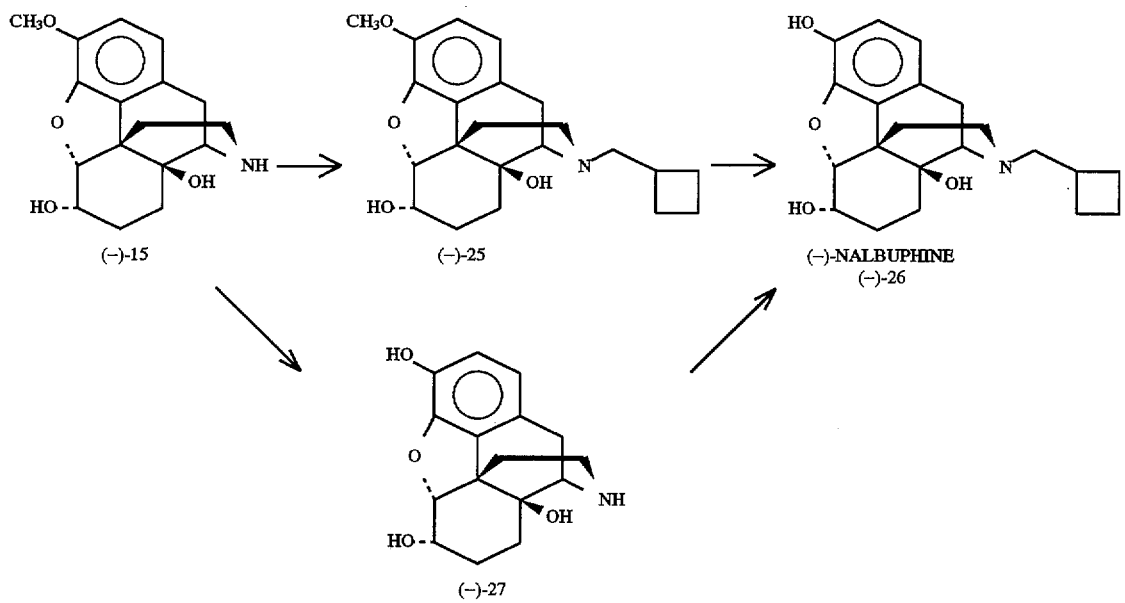

The potent narcotic agonist Foxy which is useful in pharmacological studies can also be obtained, as shown in Chart 5 below, from (−)-(14) by hydrogenation in the presence of formaldehyde to (28), previously converted to Foxy (29). Hydrogenation of (14) to (15) followed by N-methylation of (15) gives (28) the same intermediate to Foxy. The potent narcotic antagonist cyclofoxy (30), when labeled with [$^{18}$F], was recently shown to be a highly useful agent for labelling opiate receptors in the living brain by positron emission tomography. This compound is easily available from (15) by N-cyclopropylation to (31) which is O-demethylated to the corresponding 6α-naltrexol (32) and treated as previously described by the prior art. Alternately, conversion of (27) to the N-cyclopropylmethyl derivative affords the same intermediate naltrexol. Previously, the naltrexol was prepared by borohydride reduction of naltrexone and required chromatographic fractionation to remove the corresponding 6-beta-isomer.

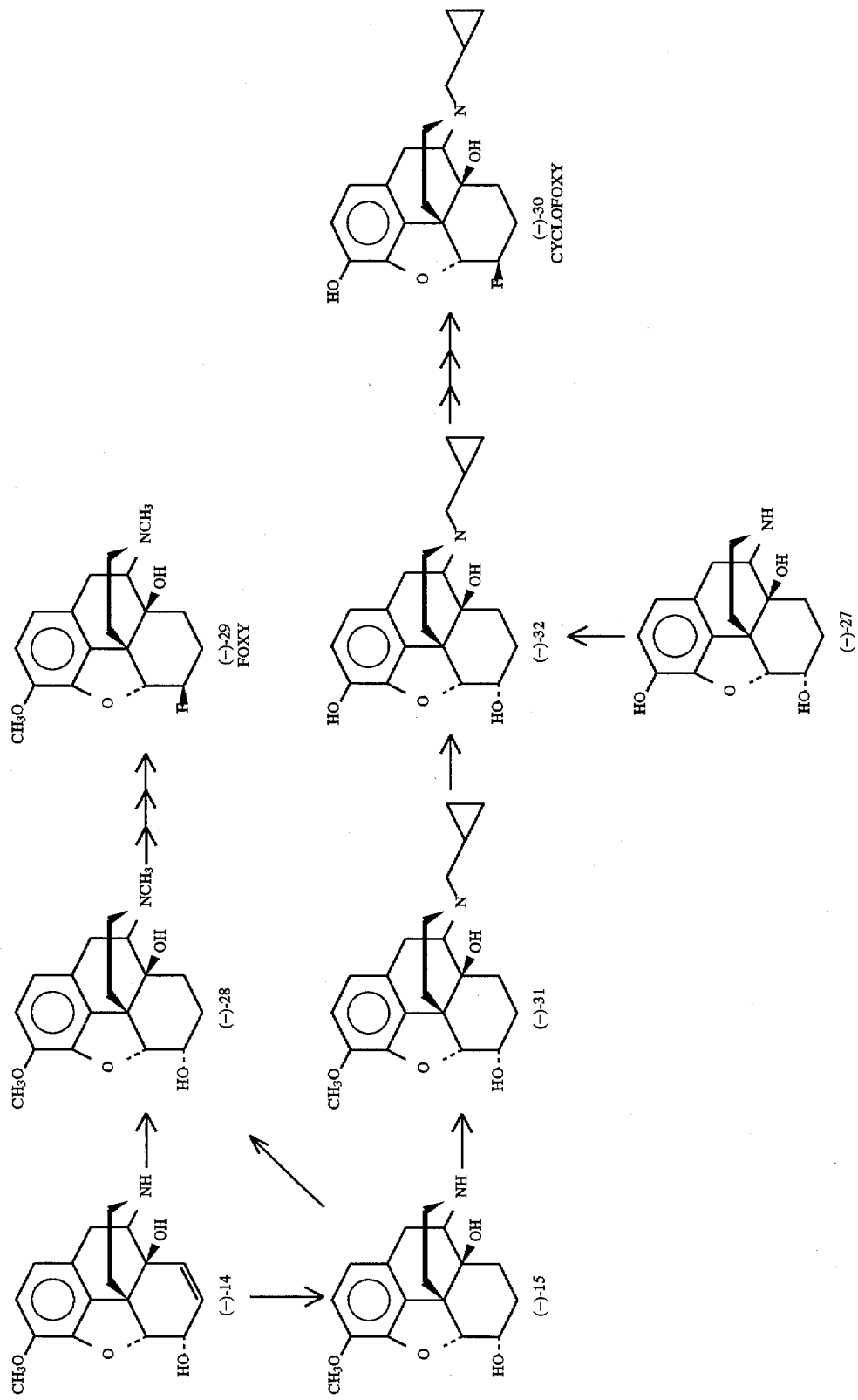

An additional utility of the instant invention is that it renders N-alkylnorthebaines including thebaine (8) readily available by total synthesis in either the natural or unnatural series by simple alkylation or reductive alkylation of the appropriate enantiomer of northebaine (12) as shown in Chart 6 below. For example, treatment of northebaine with cyclopropylmethylbromide gives cyclopropylmethylnorthebaine (33), an intermediate useful for synthesis of buprenorphine (34), a state of the art agonist antagonist drug which is effective by sublingual administration. The potent antagonist diprenorphine (35) can also be prepared from N-cyclopropylmethylnorthebaine by prior art procedures which were demonstrated only in the natural stereochemical series.

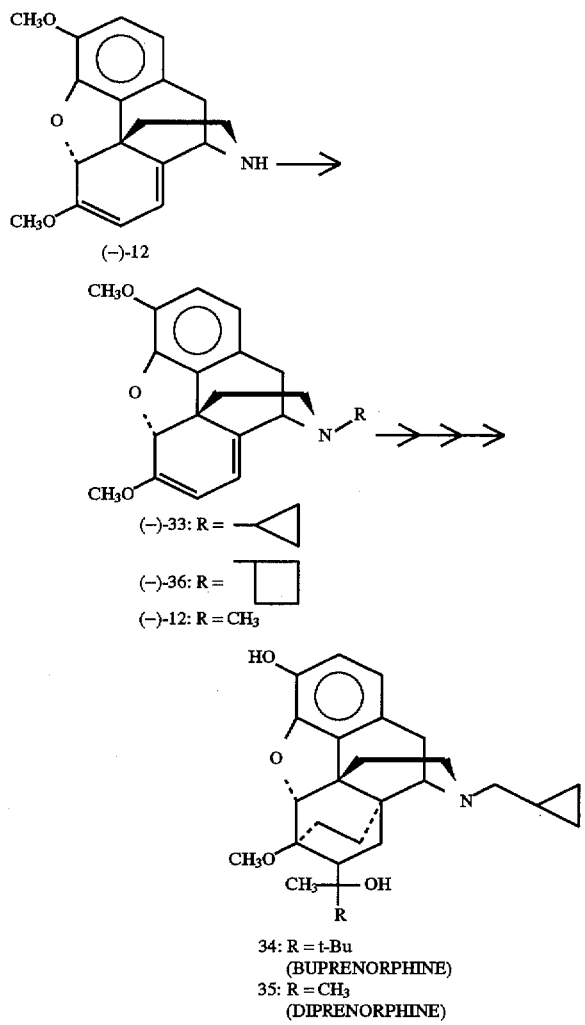

CHART 6: SYNTHESIS FROM NORTHEBAINE (12)

It is thus clear that the instant invention is an extremely practical thebaine-free total synthesis of all clinically used 14-hydroxymorphinans and other (−)-thebaine derivatives, such as (34) and (35), as well as other important compounds derived from opium. The process is shorter and more flexible than total synthesis through thebaine and is also applicable to synthesis of the unnatural opiate series (not available from opium derivatives), some members of which are potent antitussives.

Applicability of the Process for Utilization of Natural Thiamine for Semisynthetic Production of Drugs As discussed above, the instant invention eliminates requirements for thebaine for the production of medically useful drugs by total synthesis. The process is, however, applicable to synthesis of drugs from opium derived starting material via semisynthetic northebaine since northebaine is an intermediate in the invention and existing methodology developed by others permits facile, high-yielding synthesis of (−)-northebaine from natural thebaine.

The instant invention can also be used to prepare codeine (6), morphine (7), and related compounds via norcodeine (39) and normorphine (42) in both the natural and unnatural opiate series. In this sequence as shown in Chart 7 below, the norbromoketal (11) is treated with a strong base for example an organic base such as potassium t-butoxide, or sodium hydroxide or sodium amide, in an ether or hydrocarbon solvent such as tetrahydrofuran to give norcodeinone ketal (37). Hydrolysis to norcodeinone (38), followed by reduction, e.g. with sodium borohydride or other alkali butoxide, gives norcodeine (39). O-demethylation of norcodeine with BBr$_3$ e.g., then gives normorphine (42). N-methylation of (39) and (42) provides codeine (6) and morphine (7), respectively, as either the natural or unnatural isomers, depending upon the absolute configuration of (11). Codeine can also be obtained from norcodeinone (38) by treatment with formaldehyde and sodium borohydride or cyanoborohydride. Codeine can also be obtained by reductive alkylation of norcodeine with formaldehyde and borohydride.

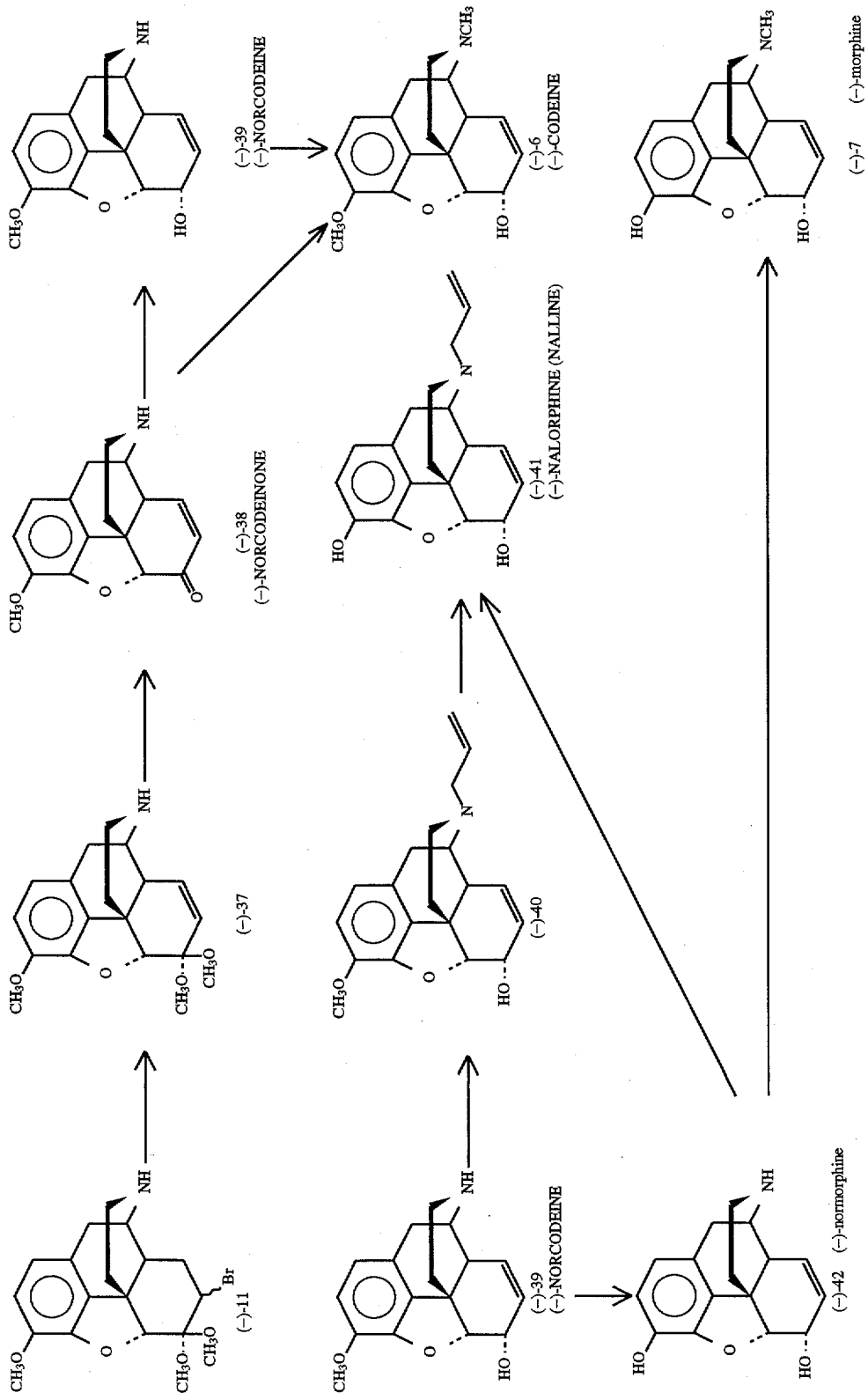

As an example of the utility of (39) and (42), nalorphine 3-O-methyl ether (40) and nalorphine (41, Nalline) can be obtained by alkylation with allyl bromide under standard conditions. Treatment of 40 with BBr$_3$ also gives nalorphine (41), a clinically used narcotic antagonist.

Preferred Embodiments

The preferred embodiment of the invention, which takes us (when R is methyl) from nordihydrocodeinone(4) to northebaine(12), 14-hydroxynorcodeinone(13) and the dimethyl ketal of norcodeinone (37a), without having to alkylate or dealkylate the secondary amine nitrogen atom is shown on Chart 8. Note that the designated names for compounds 9, 10, 11 and 12 in chart 8 correspond to the chemical structures when R is a methyl group. Nordihydrocodeinone (4) is converted first into compound (10) which may then be used to synthesize northebaine (12) and derivatives, such as the compounds of formula (37a), wherein R is a $C_1-C_8$ alkyl, preferably a $C_1-C_4$ alkyl, and most preferably a methyl group.

a mixture of compounds (9) and (10), wherein R is defined above. The R in CH(OR)$_3$ is the same as the R in ROH.

Part 2 of reaction step I is the conversion of all of compound (9) into desired compound (10). This is achieved by driving the alcohol ROH out of the reaction mixture and forcing the equilibrium reaction to favor production of compound (10). The alcohol can be removed from the reaction mixture by distillation with a solvent with a higher boiling point than the alcohol. Note that when R is a methyl group, the methyl alcohol is removed by adding anhydrous tetrahydrofuran (THF) and distilling. Azeotropes may also be formed in order to remove the ROH. For example, if ROH is ethyl alcohol, benzene can be added to form the low boiling benzene/ethyl alcohol azeotrope. Other conventional methods of removing alcohols, such as for example those employing molecular sieves, may also be used. It is noted that during the conversion of compound 4 into compound 10, an alkysulfonic ester (an undesirable alkylating agent) forms by reaction of the phenolic sulfonic acid and the trialkyl orthoformate (see Padmapriya et al., below, who describes the reaction forming the undesirable alkylating

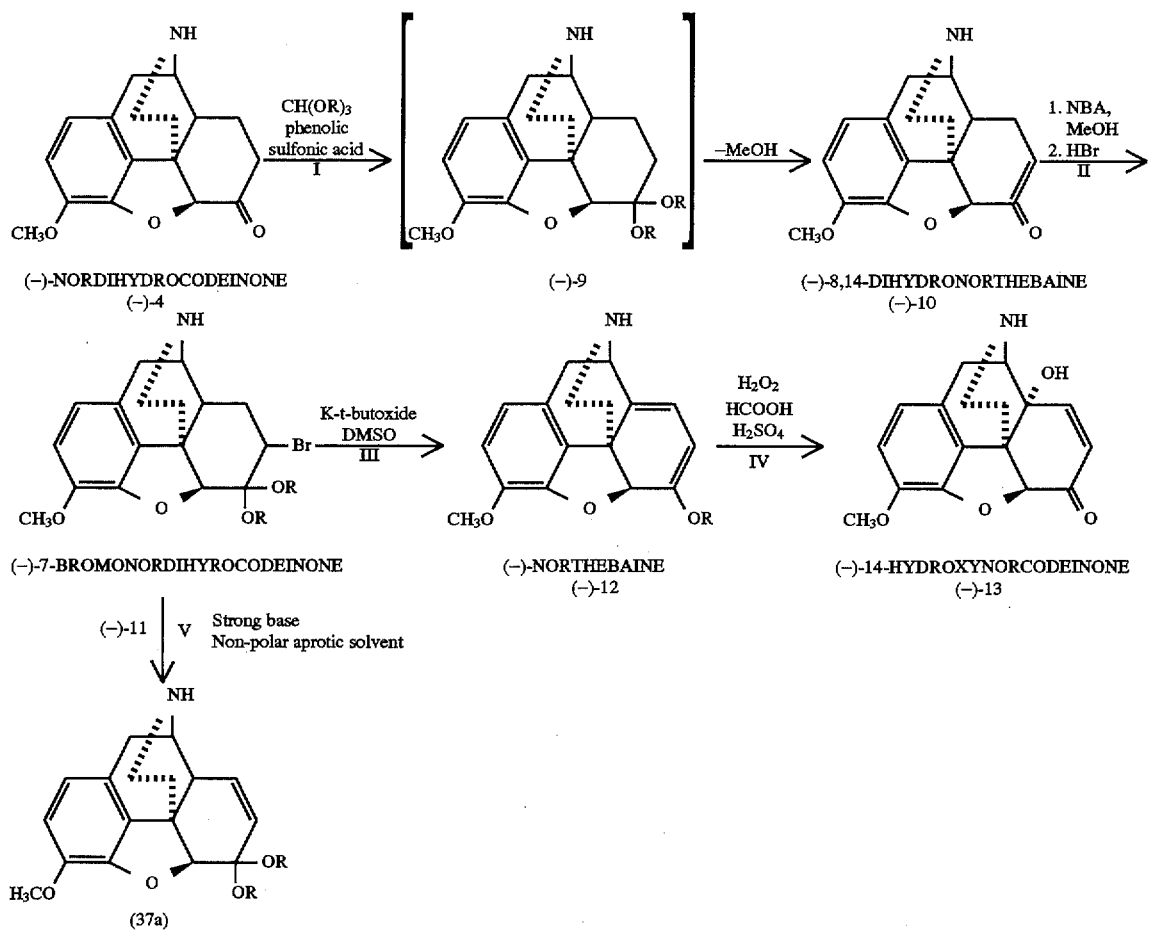

CHART 8: SYNTHESIS OF NORTHEBAINE AND NORCODEINONE DIMETHYL KETAL (ILLUSTRATED IN UNNATURAL SERIES)

Generally, reaction step I of the synthesis scheme shown in Chart 8 may be broken into three parts. Part 1 is the reaction of nordihydrocodeinone (4) with a trialkyl orthoformate CH(OR)$_3$, an alcohol ROH and a phenolic sulfonic acid, such as 5-SSA (5-sulfosalicylic acid) in order to obtain agent). This alkylating agent could alkylate the amine nitrogen atom if it came in contact with unprotonated amine (i.e., amine in neutral or basic solution). Such an alkylation would negate the advantage of the method, which is to carry out all the reactions in the N-Nor series.

Part 3 of reaction step I in Chart 8 is the addition of at least an aqueous base to form a two phase system consisting of the aqueous base and an immiscible organic solvent. The immiscible organic solvent can be the solvent left after Part 2 is completed, and/or can be added with the aqueous base. Compound (10) dissolves in the organic phase and the acid and the undesirable alkylating agent dissolves in the aqueous phase, where the latter is degraded by hydroxide ion. The presence of the phenolic hydroxyl group allows the alkylating agent to dissolve in the aqueous phase and not the organic phase. Since the addition of the base deprotonates the salt form of the amine group of compound (10), it is no longer protected from the alkylating agent by protonation. Since the alkylating agent is in a separate phase (aqueous phase) from that of compound (10) (organic phase), these two compounds cannot react to produce an undesirable alkyl group on the amine group of compound (10). Further, if conventional acids such as p-toluene sulfonic acid (see Example 3 of U.S. Pat. No. 4,613,668) or methane sulfonic acid (see Padmapriya et al., "A new method for the esterification of sulphonic acids,", *Synthetic Communications*, 15 (12) (1985), pp. 1057–1062) were used, the alkylating agents formed in the reaction would disadvantageously dissolve in the organic phase and alkylate the amine group of compound (10). This has been observed in the inventor's laboratory. Thus, sulfonic acids not containing a phenolic hydroxyl group and not soluble in water, cannot be used in this process. However, the use of phenolic sulfonic acids avoids the problem of alkylation of the amine group and is thus advantageous. Below is a discussion of the preferred reactants and reaction conditions for the reaction steps in the synthesis scheme illustrated in Chart 8.

Reaction I in Scheme of Chart 8

In reaction I illustrated in Chart 8, the phenolic sulfonic acid employed may be:

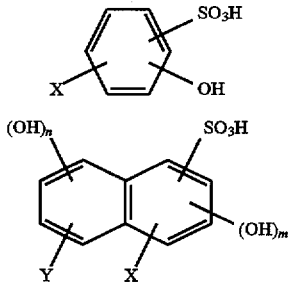

In formulas (i) and (ii), X and Y can be, independently, hydrogen, hydroxyl, halogen, COOH, lower alkyl, phenyl or any other group that does not interfere with the reaction, and which results in the alkylating agent dissolving in the aqueous phase formed in part 3 of Reaction I. The subscripts n and m are each 1 or zero but are not the same. The most preferred acid is 5-sulfosalicylic acid.

The reaction is run in a solvent consisting of the trialkylorthoformate and ROH under anhydrous conditions and under an inert atmosphere that excludes oxygen, such as for example under nitrogen, argon, etc. The reaction is run at a temperature of from room temperature (about 25° C.), and lower, as long as the solvent is still liquid, and up to the boiling point of the solvent mixture.

In forming the aqueous base/immiscible organic solvent phases, the base used is any strong hydroxide base, including alkali metal and alkaline earth hydroxides, wherein the preferred hydroxides are those of Na, Li, K, and Ca. The solvent is any organic solvent that is immiscible with water, is capable of dissolving compound (10) and does not cause any side reactions. Preferred solvents include THF and polar halogenated organic solvents. Examples of polar halogenated organic solvents include chloroform, methylene chloride, tetrachloroethylene; most preferred is chloroform.

The amount of base may be in the range from a slight molar excess over the phenolic sulfonic acid, enough to neutralize it, to a three-fold excess over the acid. In any event, the pH of the aqueous phase should be at least about 10.5, in order to dissolve the phenolic sulfonic acid and alkylating agent in the aqueous phase and away from compound (10).

Compound (10) is removed from the chloroform solvent simply by evaporating off the solvent, so that pure crystals result. The overall yield of reaction I is almost 100% of chromatographically pure product.

Reaction II in Scheme of Chart 8

This reaction converts compound (10) to compound (11). It is divided into two parts. The first part is the formation of compound (11), and the second part is the formation of its HBr salt. This reaction step may be illustrated as shown below.

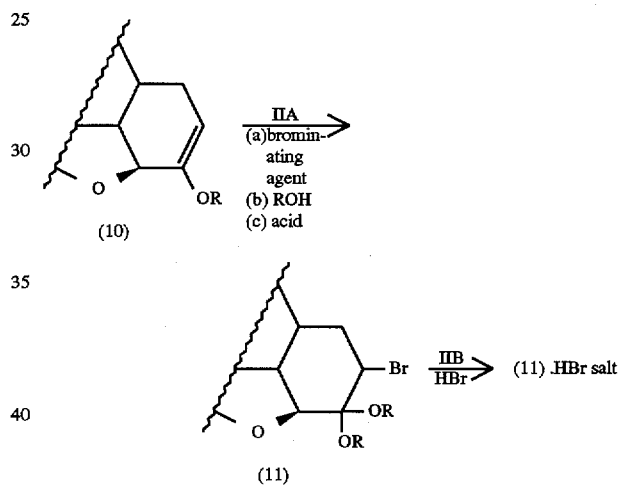

In the above step IIA, the acid is needed to help dissolve compound (10). Step IIA is surprisingly unexpected, since it is expected that a brominating agent would also brominate the phenyl ring, (see Fieser & Fieser, "Reagents in Organic Synthesis" 2, 39; and J. Org. Chem. 33 1655, 1968). It is also unexpected that the amine group is not brominated (see *Chemistry of Carbon Compounds*, Vol. 1, Part A, editor E. H. Rodd, (1951), p. 393).

Step IIB is the formation of a HBr salt of compound (11). This salt is the first known example of a stable crystalline salt of this compound.

The brominating agent used is either N-bromoacetamide (NBA) or N-bromosuccinimide, NBA being preferred. The acid used is any acid which forms a soluble salt of compound (10) in the alcohol solvent, and preferred are alkylsulfonic acids, most preferred being methane sulfonic acid. The significant molar ratios relative to compound (10) are: close to 1:1 for the brominating agent to help minimize side reactions, and from about 1:1 to 2:1 for the acid over compound (10). ROH is the solvent. The reaction is run at a temperature between −10° C. to room temperature, preferably 0° C. All solvents are anhydrous and the reaction is run under an inert atmosphere, excluding water and oxygen.

After the reaction is complete, an excess amount (relative to the acid) of aqueous ammonium hydroxide is added. The resulting mixture is extracted with chloroform or any immiscible solvent mentioned above. The chloroform is evaporated away, compound (11) is dissolved in methanol and a slight molar excess of Hbr in methanol is added. Pure crystals of compound (11) precipitate out. Unbrominated compound (10) and overbrominated compound (10) do not crystallize out. Thus, this method not only produces a crystalline salt of compound (11) (the first crystals of (11) ever produced) but the process also produces these crystals in pure form.

Reaction III in Scheme of Chart 8

This reaction results in the synthesis of northebaine (12). Compound (11) is mixed with a strong base and dissolved in a polar aprotic solvent. The success of this reaction step is surprisingly unexpected, since it is expected that a side reaction between the secondary amine and the bromine substituent to form dimers would occur under these reaction conditions (see March, *Org. Chemistry, Reactions, Mechanisms, and Structure*, 3rd ed., John Wiley & Sons, pp. 364–365), although this does not happen in reaction step III. Reaction step III is also advantageous in that it results in the production of compound (12) in only one step, whereas conventional techniques require two steps. For example, in one conventional technique, (see Bartels-Keith, *J. Chem. Soc.*, (C), (1966), pp. 617–624) the reaction is conducted in two steps: (1) reaction with t-butoxide/toluene, eliminating HBr to give one double bond and (2) reaction with acid to give the other. Finally, it is unexpected that using a polar aprotic solvent would lead to the product (12) and that if a nonpolar aprotic solvent is used another product is obtained (see reaction step V discussed below).

The strong bases used in reaction step III are exemplified by tertiary alkoxides, such as alkoxides of t-butyl or t-amyl alcohol (all alkali and alkaline earth compounds), hydrides and amides (all alkali and alkaline earth compounds). Preferred bases are t-butoxides and hydrides of, Na, K and Li. Most preferred as a base is K t-butoxide. The solvent must be a polar aprotic solvent, since nonpolar solvents will result in the wrong product. Examples are dimethylsulfoxide (DMSO), dimethyl formamide (DMF) and hexamethyl phosphonic triamide. The reaction is run between 0° C. and 80° C., preferably 30°–60° C., in anhydrous conditions under an inert atmosphere that excludes water and oxygen. The base is present in a 2:1 to 12:1 molar excess over compound (11). The solvent volume is kept as small as possible while still dissolving the reactants.

Compound (12) is isolated from the reaction mixture by adding water and extracting with an immiscible organic solvent (preferably chloroform) as described above. This solvent is evaporated and compound (12) is crystallized from methanol.

Reaction IV in Scheme of Chart 8

This reaction is the formation of 14-hydroxynorcodeinone, i.e. compound (13). The result of this reaction is surprisingly unexpected, since it is expected that the hydrogen peroxide employed therein would react with the amine group to form a HO—N= group. (See Patai (ed.), *The Chemistry of the Amine Group*, (1968), John Wiley & Sons, New York, pp. 325–326). However, this does not occur in reaction step IV.

The $H_2O_2$ and HCOOH employed in step IV give performic acid (HCOOOH), this reaction being catalyzed by the sulfuric acid. Other oxidizing agents which may be used include peracetic acid, perphthalic acid, dichromate and ozonolysis. The reaction occurs in a water/formic acid medium, at a temp of 0° C.–50° C., preferably room temperature, open to the atmosphere.

Reaction V in Scheme of Chart 8

This reaction produces the norcodeinone dialkyl ketal (derivatives 37a), a valuable intermediate. The strong base used is the same as that used in reaction III above. The solvent must be a non-polar aprotic solvent. Examples are tetrahydrofuran and carbon tetrachloride, THF being preferred. The reaction is run at a temperature ranging from room temperature up to the reflux temperature of the solvent, 65° C. for THF. Other solvents may be used at a temperature of between room temperature and 80° C. The reaction is run under anhydrous and inert atmosphere conditions. The base is present in molar excess, preferably between 2:1 and 12:1 compared to compound (11). The concentration in the solvent varies between 1 and 10% by weight, preferably about 5%. The compound is isolated by crystallizing from a water/THF mixture.

EXAMPLES

Melting points were determined on a Thomas-Hoover melting point apparatus and are corrected. Elemental analyses were performed by Atlantic Microlabs, Atlanta, Ga. IR spectra were determined on a Beckman IR 4230 spectrophotometer; mass spectra (chemical ionization, $NH_3$) were obtained on a Finnegan 1015 spectrometer ($NH_3$-CI) and $^1$H-NMR were obtained on Varian XL 300 or Varian 220 NMR spectrometers. Optical rotations were measured with a Perkin-Elmer Model 241 polarimeter. Silica gel GF plates (Analtech, Newark, Del.) were employed for thin layer chromatography (TLC) and a Hewlett Packard 5880A gas chromatograph with a 6-ft methyl silicone column was used for capillary gas chromatography (GC). Acidification of non-aqueous solutions in some cases was monitored by application of an aliquot to moist pH indicator sticks (E. Merck). TLC and GC were used to compare all enantiomeric compounds throughout the synthesis and as criteria for purity. All synthesized products had Rf values and retention times which were identical with those of their authentic (−)-enantiomers. All other spectral data obtained on each (+)-enantiomer were identical to that of authentic (−)-enantiomers with the exception of opposite optical rotation.

Applicability of the Present Invention to the Natural or Unnatural Opiate Series The following examples beginning with (+)nordihydrocodeinone ((+)-4) illustrate the instant invention in the unnatural (+)-opiate series but in no way imply limitation to the (+)-series. For synthesis of the (−)-compounds with the natural opiate absolute configuration of the carbon nitrogen skeleton, it is merely necessary to employ (−)-nordihydrocodeinone ((−)-4) in an exact replication of the process. In this manner, the (−)-enantiomers described above are obtained which are identical in every respect with authentic samples prepared by classical routes from opium. Obviously, (−)-northebaine prepared by N-demethylation of natural (−)-thebaine could be utilized instead of the identical substance prepared by total synthesis.

Example 1

(+)-8,14-Dihydronorthebaine, [(+)-10]

A solution of 22.8 g 5-sulfosalicylic acid (90 mmol) in 8 mL MeOH was added to 38 g trimethyl orthoformate (352 mmol) in 8 mL MeOH and allowed to stir at reflux for 5 min, under an atmosphere of argon. A solution of 22.8 g (64 mmol) of anhydrous (+)-nordihydrocodeinone [-4] in 30 mL MeOH was added dropwise at a constant rate to the refluxing reaction mixture via addition funnel over 1 h. If the addition is too rapid the insoluble salt of the starting material will crystallize and the reaction will not go to completion because of the low solubility of this salt. The addition funnel was rinsed with 10 mL dry THF and the reaction mixture stirred at reflux for 30 min at which time GC analysis of the basic fraction showed complete loss of starting material and a mixture of 90% ketal and 10% 8,14-dihydronorthebaine (10). The condenser was replaced with a fractional distillation apparatus and 30 mL MeOH was removed by distillation. The reaction mixture became cloudy, as crystals (5-sulfosalicylic acid salt of 10) separated. Dry THF was added at the rate of distillation via addition funnel; after distillation of 300 mL THF, GC (RT=4.90, 220° C.) and TLC analysis showed the reaction was complete. The reaction mixture was poured, under an atmosphere of argon, into 150 mL of vigorously stirred 10% NaOH, at 0° C., and allowed to stir for 5 min; the reaction flask was washed with 30 mL THF. Removal of the residual THF in vacuo (leaving a two phase system consisting of the product and the aqueous phase), followed by extraction with 1×100 mL and 2×50 mL $CHCl_3$ then washing the combined organic extract with 1×50 mL $H_2O$ and removal of volatiles in vacuo resulted in a brown syrup. Crystallization from EtOAc afforded 17.09 g (90%) of (+)-10; mp 148.5°–150.5° C. (mp lit 152°–152.5° C.) which was homogeneous and identical to the (−)-enantiomer by TLC and homogeneous by TLC and GC analysis (220° C.). Anal. calc. for $C_{18}H_{21}NO_3$: C, 72,26; H, 7.02; N, 4.64. Found: C, 72.16; H, 7.12; N, 4.64. $[\alpha]_D^{28}$+217.6 (c, 1.27, $CHCL_3$).

Example 2

(+)-7-Bromonordihydrocodeinone Dimethyl Ketal Hydrobromide, [(+)-11].HBr

A solution of 27.0 g (+)-10 (90 mmol) in 400 mL MeOH was mechanically stirred at 0° C. under an atmosphere of argon. A solution of 9.45 mL methanesulfonic acid (126 mmol) in 75 mL MeOH was added and the reaction mixture was allowed to stir at 0° C. for 10 min. N-bromoacetamide (NBA; 11.2 g, 81 mmol) was slowly added portionwise to the reaction mixture. After stirring for 20 min, 1.0 g NBA (6.3 mmol) was added followed by 20 min stirring and an additional 250 mg NBA (1.8 mmol). After 10 min additional stirring, the reaction was complete by GC and TLC analysis. Saturation with $NH_3$ gas to pH 9.5 followed by removal of MeOH, in vacuo, resulted in a yellow syrup. The mixture was treated with 200 mL of 20% $NH_4OH$ and extracted with 3×100 mL of $CHCl_3$. The organic phase was washed with 100 mL 20% $NH_4OH/H_2O$ and evaporated to a syrup. Distillation of toluene followed by isooctane, and drying in high vacuum gave 37.55 g of off-white foam that was 95% pure by GC analysis. This material was dissolved in 40 mL hot MeOH and acidified with freshly prepared HBr/MeOH. Cooling to 0° C. gave 38.1 g of white crystalline (+)-11.HBr (88%), mp 232° C. Anal. calc. for $C_{19}H_{24}NO_4$.HBr: C, 46.47; H, 5.09; N, 2.58. Found: C, 46.30; H, 5.18; N, 2.80. $[\alpha]_D^{28}$+116.0 (c 1.06, $CHCl_3$).

Example 3

(+)-Northebaine, [(+)-12]

To a mixture of potassium t-butoxide (9.0 g, 83.2 mmol) and 40 mL DMSO at 0° C., was added 5.0 g of (+)-11 free base (10.4 mmol) and allowed to stir at room temperature. The orange reaction mixture was gently warmed to 45° C. and after 30 min, GC analysis showed complete loss of starting material. After 2 h, 2.25 g potassium t-butoxide was added (20.8 mmol) and the reaction was completed in 15 min. The reaction mixture was cooled to 0° C., quenched with 100 mL $H_2O$ and extracted with 3×100 mL $CHCl_3$. The organic phase was washed with 50 mL $H_2O$ and evaporated to a yellow syrup. Addition and evaporation of MeOH gave crystalline product: 2.87 g (97%), mp 157°–158° C., lit. Bartels-Keith, *J. Chem. Soc. (C)*, 1966, 617–624, mp for (−)-12, mp 157°–159° C. Anal. Calc. for $CF_{18}H_{19}NO_3$: C, 72.74; H, 6.39; N, 4.71. Found: C, 72.60; H, 6.48; N, 4.65. $[\alpha]_D^{28}$+235.2 (C, 1.08, $CHCL_3$).

Example 4

(+)-14-Hydroxynorcodeinone, [(+)-13] (+)—

Northebaine [(+)-12](14.8 g, 50 mmol) was added to a solution of 6.5 mL 88% formic acid and 26 mL 0.7% sulfuric acid, followed by addition of 7.2 mL 30% $H_2O_2$. The resulting heterogeneous reaction mixture became homogeneous and golden brown and was allowed to stir at room temperature for 48 h. Neutralization with 120 mL 10% $Na_2CO_3$ (pH 9.5) gave crystalline material that was filtered and washed with 50 mL $H_2O$ and 100 mL MeOH to give 12.1 g (81%) cream-colored crystalline product. The aqueous filtrate was saturated with NaCl, extracted with 4×100 mL $CHCl_3$/MeOH (9:1). Evaporation of the extracts in vacuo and crystallization in MeOH resulted in 1.3 g (9%) crystalline product. Recrystallization of the combined material gave 13.4 g (90%) product which was homogeneous by TLC; mp 209°–210° C. Anal. calc. for $C_{17}H_{17}NO_4$·3/4 $H_2O$: C, 65.29; H, 5.92; N, 4.47. Found: C, 65.12; H, 6.02; N, 4.45. $[\alpha]_D^{25}$+171.73 (10.4, $CHCl_3$).

Example 5

(+)-Noroxycodone [(+)-18]

Catalytic hydrogenation of (+)-13 (4.5 g, 15 mmol) in 90 mL 10% glacial acetic acid (w/w) and 500 mg 5% Pd/BaSO$_4$ was followed by filtration over celite and washing the filter pad with 100 mL glacial acetic acid and 100 mL 10% glacial acetic acid. Neutralization of the filtrate with $NH_4OH$ to pH 9.5 and extraction with 3×50 mL $CHCl_3$ and 3×50 mL $CHCl_3$/MeOH 9:1 followed by removal of volatiles, in vacuo, resulted in a white powder 4.5 g (100% crude) that was 98.8% pure by GC analysis. Purification by preparation of the HI salt, in MeOH followed by recrystallization with MeOH/ether gave the HI salt of (+)-18 which was homogeneous by TLC. Anal. calc. for $C_{17}H_{19}NO_4$.HI: C, 47.58; H, 4.66; N, 3.26. Found: C, 47.55; H, 4.74; N, 3.23.$[\alpha]_D^{25}$+100.4 (C. 0.55, MeOH).

Example 6

(+)-Noroxymorphone [(+)-19]

O-Demethylation of (+)-18 was performed, dissolving 150 mg of (+)-18 (0.5 mmol) in 1.5 mL $CHCl_3$ and adding the solution to a stirring mixture of $BBr_3$ (0.3 mL, 30 mmol) in 1.5 mL $CHCl_3$ at 0° C. The pale yellow heterogeneous reaction mixture was allowed to stir at 0° C. for 20 min and at room temperature for 40 min. The reaction was quenched by pouring onto 4 g ice/2 mL $NH_4OH$ (pH 9.5) and was allowed to stir at 0° C. for 30 min. The white crystalline material was filtered, washed with 10 mL cold $H_2O$ and 10 mL cold CHCl$_3$, and dried in a vacuum oven over night. The crystalline (+)-19, 80 mg (60% yield), was homogeneous and identical to authentic (−)-noroxymorphone by TLC, mp d >260° C., mp (−)-noroxymorphone d >260° C., MS (CI) M+1 288, (HCl salt). The HCl salt of (+)-19 was formed in MeOH and gave (+)-19HCl which was homogeneous by TLC, mp >260° C. $[\alpha]_D^{22}$+126.95 (C, 0.82, MeOH).

Example 7

(+)-Naloxone-3-O-methyl Ether.HCl [(+)-23.HCl]

A mixture of 2.1 g of (+)-18 (7 mmol), 21 mL dry DMF and 4.9 g anhydrous K$_2$CO$_3$ (35 mmol) was allowed to stir at 0° C. Allyl bromide (0.7 mL, 8 mmol) was added and the heterogeneous reaction mixture was allowed to stir at 0° C. for 10 min and room temperature for 1.5 h. The inorganic material was removed by suction filtration and washed repeatedly with a total of 50 mL CHCl$_3$. The filtrate was then washed with 3×10 mL 10% Na$_2$CO$_3$ and 1×10 mL H$_2$O; evaporated in vacuo to a clear syrup, then dried on a vacuum pump at 50° C., resulting in 2.2 g white foam (92% crude). The crude product was dissolved in a minimum volume of hot 2-propanol and acidified to pH >2 with HCl/2-propanol. Crystallization and recrystallization in 2-propanol gave 2.8 g of (+)-23.HCl (86%) mp 248°–250° C. Anal. calc. for: C$_{20}$H$_{23}$NO$_4$.HCl.1/2 H$_2$O: C, 62.12; H, 6.21; N, 3.62. Found: C, 62.34; H, 6.49; N, 3.62. $[\alpha]_D^{22}$_176.11 (C, 0.95, MeOH).

Example 8

(+)-Naloxone [(+)-20]

Conversion of 680 mg of (+)-23.HCl (1.8 mmol) to the free base was performed in the usual manner, neutralize with NH$_4$OH (ph 9.5), and extract with CHCl$_3$. The dry, foamy free base was dissolved in 5 mL CHCl$_3$ and added dropwise to a stirring solution of 1.0 mL BBr$_3$ (10.7 mmol) in 5 mL CHCl$_3$ at 0° C. The addition funnel was washed with 2 mL CHCl$_3$ and the reaction mixture was allowed to stir t 0° C. for 40 min then room temperature for 20 min. The reaction was quenched by pouring onto 15 g ice/4 mL NH$_4$OH (pH 9) and allowed to vigorously stir at 0° C. for 30 min. The organic layer was removed and the aqueous layer extracted with 4×10 mL CHCl$_3$. The organic fractions were combined and washed with 2×10 mL brine and 2×10 mL H$_2$O. Volatiles were removed in vacuo to give 450 mL white solid (80% crude). The crude product crystallized and was recrystallized in hot EtOAc to give 300 mg crystalline (+)-20 (60%), mp 167°–168° C. The free base was converted to the hydrochloride salt by dissolving in a minimum volume of 2 propanol and accordingly to pH 2 with HCl/2-propanol. Recrystallization in absolute ethanol gave (+)-20:HCl as white crystals, mp 206°–210° C., lit. Merck Index, 10th ed., 1983 or (−)-2 0:HCl, mp 200°–205° C. Anal. Calc. C$_{19}$H$_{21}$NO$_4$:HCL:2H$_2$O: C, 57.10; H, 6.51; N, 3.50. Found: C, 57.07; H, 6.37; N, 3.37 $[A]_D^{22}$+148.6 (0.97, MeOH).

Example 9

(+)-Naltrexone-3-O-methyl Ether.HCl.1 Isopropanol-[(+)-24]

A heterogeneous solution of 5.57 g of (+)-18 (18.5 mmol), 50 mL dry DMF and 13.0 g anhydrous K$_2$CO$_3$ (92.5 mmol) was allowed to stir at 0° C. Bromomethylcyclopropane (2.2 mL, 22 mmol) was added and the heterogeneous reaction mixture was allowed to stir at 0° C. for 10 min, then for 24 h at room temperature. The inorganic material was removed by suction filtration and washed with 200 mL CHCl$_3$. The filtrate was washed with 3×100 mL 10% aqueous Na$_2$CO$_3$ and 100 mL H$_2$O and the volatiles were removed in vacuo. Distillation of toluene and drying at 50° C. in high vacuum gave a white foamy product, 5.9 g (90% crude). The free base was converted into the hydrochloride salt by dissolving in a minimum volume of hot 2-propanol and acidifying to pH 2 with HCl/2-propanol. Crystallization and recrystallization gave 7.0 g (84%) of (+)-24.HCl.1 isopropanol white crystalline salt; mp 235°–238° C. Anal. Calc. C$_{21}$H$_{25}$NO$_4$: HCl:3/2 H$_2$O: C, 60.23; H, 6.93; N, 3.34. Found: C, 60.41; H, 6.89; N, 3.34.

Example 10

(+)-Naltrexone [(+)-21]

Conversion of 2.35 g (+)-24.HCl isopropanol into the free base was performed by extraction from 10% aqueous Na$_2$CO$_3$ into CHCl$_3$ to give 2.1 g of white foamy free base which was dissolved in 18 mL CHCl$_3$ (dried over 3A molecular sieves) and added dropwise to a stirring solution of 3.5 mL BBr$_3$ (freshly distilled over Hg) and 18 mL CHCl$_3$ at 0° C. The addition funnel was washed with 7 mL CHCl$_3$ and the reaction was allowed to stir for 20 min at 0° C. and 45 min at room temperature. The reaction mixture was quenched on 53 g ice/18 mL NH$_4$OH (pH 9.5) and after washing the reaction flask with aqueous NH$_4$OH/CHCl$_3$, it was allowed to stir for 30 min at 0° C. The aqueous mixture was extracted with 4×30 mL CHCl$_3$ and the organic phase was washed with 2×30 mL H$_2$O and 2×50 mL brine, dried (Na$_2$SO$_4$) and the volatiles were removed in vacuo resulting in 1.8 g white foam (88% crude). Crystallization and recrystallization in EtOAc gave 1.15 g of (+)-21 white crystals (57%); mp 155° C. Anal. calc. for C$_{20}$H$_{23}$NO$_4$.1/4 EtOAc: C, 69.44; H, 6.88; N, 3.85. Found: C, 69.42; H, 6.88; N, 4.00.$[\alpha]_D^{22}$+194.51 (C, 0.82, MeOH).

Example 11

(+)-Nalmefene.HCl [(+)-22.HCl]

This compound can be prepared from (+)-naltrexone [(+)-21] as described by Hahn, et al., *J. Med. Chem.*, 1975, Vol. 18, pp 259–262, for the (−)-isomer. The (+)-compound showed mp 186°–187° C., (−)-nalmefene, mp 187°–189° C. (GC analysis showed 100% purity, RT=7.42, 220° C.). The hydrochloride salt was prepared in 2-propanol with HCl/2-propanol (pH 2), and crystallized and recrystallized in 2 propanol to give (+)-nalmefene. HCl mp 199°–200° C., lit., Hahn, et al., *J. Med. Chem.*, 1975, Vol. 18, pp 259–262, mp for (−)-nalmefene.HCl 197°–198° C. Anal. calc. for C$_{21}$H$_{25}$NO$_3$.HCl.1/2 H$_2$O: C, 65.47; H, 7.41; N, 3.45. Found: C, 65.52; H, 7.07; N, 3.63. $[c]^{22}$+1 43.7 (C, 1.05, MeOH), corrected for anhydrous +147.2 $[\alpha]_D^{22}$ (authentic (−)-145.4) (C, 1.04, MeOH).

Example 12

(+)-Norcodeinone Dimethyl Ketal [(+)-37]

Conversion of 2.5 g of (+)-11 to the free base (2.13 g foam, 4.26 mmol) was done with 20% NH$_4$OH and ether extraction followed by drying. To a solution of the free base in 42 mL dry THF, 1.15 g potassium t-butoxide (8.5 mmol) was added and the reaction mixture was allowed to stir at room temperature, under an atmosphere of argon for 24 h. GC analysis showed the reaction was complete (RT=5.17, 220° C.); the THF was removed in vacuo and 15 mL H$_2$O was added. The (+)-37 was isolated as a white feathery dihydrate (as seen in NMR analysis) 1.60 g (100%) mp 113°–114° C., lit., Bartels-Keith, *J. Chem. Soc.* (C), 1966, 617–624, for (−)-37, mp 113°–114° C. Ana 1. calc. for $C_{19}H_{23}NO_4 \cdot 3/4 H_2O$: C, 66.58; H, 7.14; N, 4.08. Found: C, 66.49; H, 7.23; N, 4.00. $_D^{28}$+215.9 (C, 1.09, $CHCl_3$).

Example 13

(+)-Norcodeine [(+)-39]

A solution of 1.0 g (+)-37 (3 mmol) in 15 mL 3N HCOOH (2.35 g 88% HCOOH in a total volume f 15 mL $H_2O$) was allowed to stir at room temperature for 20 min at which time GC analysis showed complete loss of starting material. The reaction mixture was neutralized to pH 5.5–6.0 with portionwise addition of solid $NaHCO_3$ at 0° C.[1]. Sodium borohydride (90 mg, 3.4 mmol) was added and the reaction mixture was allowed to stir for 20 min. To the completed reaction mixture, 6 mL 1.0N NaOH was added and extraction with 3×10 mL $CHCl_3$ followed by removal of solvent in vacuo resulted in a white foam which crystallized in 2-propanol to give a (+)-39. 750 mg (90%) mp 178°–181° C., d-authentic sample of (−)-39, mp 181°–183° C. Anal. calc. for $C_{17}H_{19}NO_3$: C, 71.60; H, 6.66; N, 4.91. Found: C, 71.45; H, 6.76; N, 4.84. $[\alpha]_D^{28}$+115.23 (C, 1.09, $CHCl_3$).

[1] Note the intermediate norcodeinone [(+)-38] can be isolated as a white foam by solvent extraction and evaporation.

Example 14

(+)-Nalorphine-O-methylether [(+)-40]

To a solution of 540 mg (+)-norcodeine [(+)-39] (1.9 mmol) in 6 mL dry DMF, 1.33 g $K_2CO_3$ (9.5 mmol) and 0.19 mL allyl bromide (2.1 mmol) were added at 0° C. The reaction mixture was allowed to stir at 0° C. for 10 min, then at room temperature for 50 min. Inorganic material was removed by suction filtration and washed with 10 mL $CHCl_3$. Volatiles were removed in vacuo from the filtrate which was then extracted with 3×10 mL $CHCl_3$ from 10 mL 10% $Na_2CO_3$ followed by washing of the organic phase with 10 mL $H_2O$ and evaporation of solvent. Crystallization from ether gave 445 mg white crystalline (+)-40 (72%) that was homogeneous by TLC. mp 91°–93° C., lit. *J. Am. Chem. Soc.*, 1942, 64:869, mp for (−)-40, 93° C. Anal. Calc. for $C_{20}H_{23}NO_3$: C, 73.86; H, 7.07; N, 4.31. Found: C, 73.76; H, 7.13; N, 4.28. $[\alpha]_D^{25}$+130.40 (C, 0.99, $CHCl_3$).

Example 15

(+)-Nalorphine [(+)-41]

A solution of 235 mg (+)-40 (0.72 mol) in 1.5 mL $CHCl_3$ was added dropwise over 1 min to a solution of 0.44 mL $BBr_3$ (4.3 mmol freshly distilled over Hg) in 13 mL $CHCl_3$ at 0° C. The addition funnel was washed with 1 mL $CHCl_3$ and the reaction mixture was allowed to stir at 0° C. for 20 min and room temperature for 20 min. The yellow heterogeneous reaction mixture was poured onto 6 g ice/3 mL $NH_4OH$ (pH 9.5) and allowed to stir at 0° C. for 45 min. The volatiles were removed in vacuo resulting in a gummy product which was dissolved in 5 mL $CHCl_3$ and washed with 2×10 mL 10% $NH_4OH$; the aqueous phase was then washed with 5×10 mL $CHCl_3$ and the combined $CHCl_3$ fractions were washed with 1×10 mL $H_2O$. Evaporation of solvent and distillation of toluene resulted in 300 mg crude product which crystallized in ether, to give 200 mg of (+)-41, (89%) mp 188°–191° C., lit. Merck Index, 10th ed., 1983, mp for (−)-41, 208°–209° C. Purification by formation of the hydrochloride salt in 2-propanol and recrystallization in MeOH gave 150 mg (45%) of pure HCl (+)-41 as the salt, mp d >260, lit. Merck Index. 10th ed., 1983, mp for (−)-41:HCl d 269° C. $[\alpha]_D^{25}$+99.91 (C, 1.06, MeOH).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing 14-hydroxynorcodeinone of both the natural (−) and unnatural (+) series, wherein the method for producing the unnatural (+) series compound comprises the steps of:

(a) reacting (+)-nordihydrocodeinone with a trialkylorthoformate $CH(OR)_3$, alcohol ROH and phenolic sulfonic acid to produce a first mixture containing compounds of formula (10)

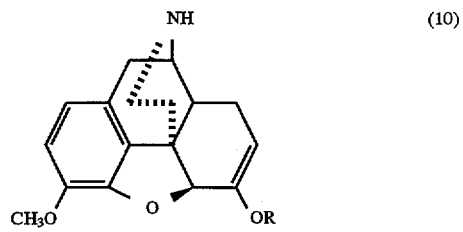

and its corresponding ketal;

(b) converting all of said corresponding ketal to said compounds of formula (10) by removing said alcohol ROH from said first mixture to form a second mixture;

(c) converting said second mixture to a two phase system by adding to said second mixture at least an aqueous base to form a two phase system having an aqueous phase and an immisible organic solvent phase, said compounds of formula (10) dissolving in the organic phase for removal therefrom;

(d) reacting said compounds of formula (10) with a brominating agent to produce compounds of formula (11)

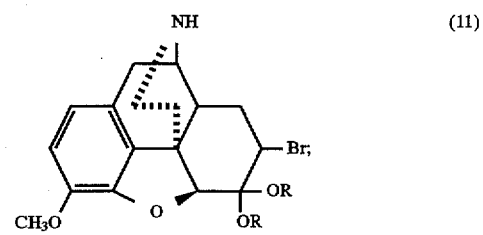

(e) reacting said compounds of formula (11) with a strong base in a polar aprotic solvent to produce compounds of formula (12)

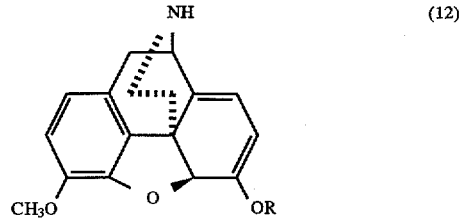

; and (f) reacting said compounds of formula (12) with an oxidizing agent to produce the compound of formula (13)

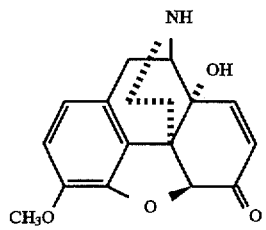

wherein R is a $C_1$–$C_8$ alkyl group.

2. The method of claim 1 for producing the unnatural (+) series compounds.

3. The method of claim 1 for producing the natural (−) series compounds, wherein the starting material is (−)-nordihydrocodeinone.

4. The method of claim 2, wherein R is a methyl group.

5. The method of claim 3, wherein R is a methyl group.

6. A method for producing northebaine compound derivatives of both the natural (−) and unnatural (+) series, wherein the method for producing the unnatural (+) series compounds comprises the steps of:

(a) reacting (+)-nordihydrocodeinone with trialkyl orthoformate $CH(OR)_3$, alcohol ROH and phenolic sulfonic acid to produce a first mixture containing compounds of formula (10)

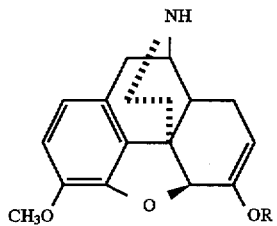

and its corresponding ketal;

(b) converting all of said corresponding ketal to said compounds of formula (10) by removing said alcohol ROH from said first mixture to form a second mixture;

(c) converting said second mixture to a two phase system by adding to said second mixture at least an aqueous base to form a two phase system having an aqueous phase and an immisible organic solvent phase, said compounds of formula (10) dissolving in the organic phase for removal therefrom;

(d) reacting said compounds of formula (10) with brominating agent to produce compounds of formula (11)

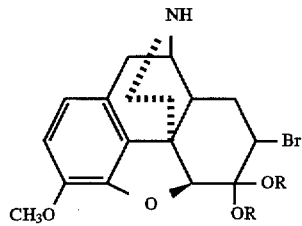

(e) reacting said compounds of formula (11) with a strong base in a polar aprotic solvent to produce compounds of formula (12)

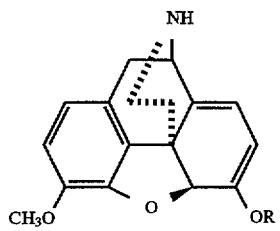

wherein R is a $C_1$–$C_8$ alkyl group.

7. The method of claim 6, for producing the unnatural (+) series compounds.

8. The method of claim 6, for producing the natural (−) series compounds, wherein the starting material is (−)-nordihydrocodeinone.

9. The method of claim 7, wherein R is a methyl group.

10. The method of claim 8, wherein R is a methyl group.

11. A method for producing 8,14-dihydronorthebaine compound derivatives of both the natural (−) and unnatural (+) series, wherein the method for producing unnatural (+) series compounds comprises the steps of:

(a) reacting (+)-nordihydrocodeinone with trialkyl orthoformate $CH(OR)_3$, alcohol ROH and phenolic sulfonic acid to produce a first mixture containing compounds of formula (10)

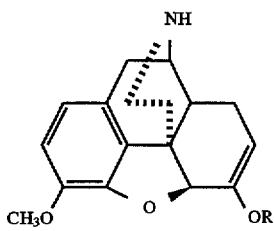

and its corresponding ketal, wherein R is a $C_1$–$C_8$ alkyl group;

(b) converting all of said corresponding ketal to said compounds of formula (10) by removing said alcohol ROH to form a second mixture; and (c) converting said second mixture to a two phase system by adding to said second mixture at least an aqueous base to form a two phase system having an aqueous phase and an immiscible organic solvent phase, wherein said compounds of formula (10) dissolve in the organic phase for removal therefrom; and wherein the method for producing natural (−) series compounds employs (−)-nordihydrocodeinone in step (a).

12. The method of claim 11 for producing the natural (−) series compounds, wherein the starting material is (−)-nordihydrocodeinone.

13. The method of claim 11 for producing the unnatural (+) series compounds.

14. The method of claim 12, wherein R is a methyl group.

15. The method of claim 13, wherein R is a methyl group.

16. A method for producing 14-hydroxynorcodeinone of the natural (−) and unnatural (+) series, wherein the method for producing the unnatural (+) series compounds comprises the step of:

reacting compounds of formula (12)

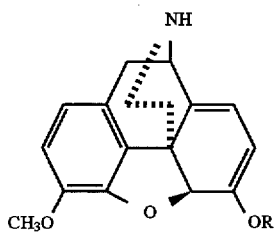
(12)

with an oxidizing agent to produce a compound of formula (13)

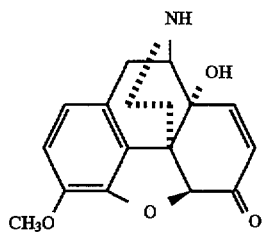
(13)

wherein R is a $C_1$–$C_8$ alkyl group.

17. The method of claim 16 for producing the natural (−) series compounds, wherein the starting compound is the natural (−) enantiomer of the compound of formula (12).

18. The method of claim 16 for producing the unnatural (+) series compounds.

19. The method of claim 17, wherein R is a methyl group.

20. The method of claim 18, wherein R is a methyl group.

* * * * *